United States Patent
Cutrell et al.

(10) Patent No.: US 10,551,940 B2
(45) Date of Patent: Feb. 4, 2020

(54) APPARATUS FOR USE IN A VIRTUAL REALITY SYSTEM

(71) Applicant: Microsoft Technology Licensing, LLC, Redmond, WA (US)

(72) Inventors: Edward Cutrell, Seattle, WA (US); Christian Holz, Seattle, WA (US); Hrvoje Benko, Seattle, WA (US); Michael J. Sinclair, Kirkland, WA (US); Meredith June Morris, Bellevue, WA (US); Yuhang Zhao, Bellevue, WA (US); Cynthia Lynn Bennett, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 103 days.

(21) Appl. No.: 15/821,713

(22) Filed: Nov. 22, 2017

(65) Prior Publication Data

US 2019/0155404 A1    May 23, 2019

(51) Int. Cl.
*G06F 3/0346* (2013.01)
*A63F 13/285* (2014.01)
(Continued)

(52) U.S. Cl.
CPC .......... *G06F 3/0346* (2013.01); *A63F 13/211* (2014.09); *A63F 13/285* (2014.09);
(Continued)

(58) Field of Classification Search
CPC .............. A63F 13/211; A63F 2300/105; A63F 2300/1062; G06F 2203/012; G06F 3/011; G06F 3/0487; G06F 3/0346; G06F 3/0356
See application file for complete search history.

(56) References Cited

U.S. PATENT DOCUMENTS

| 5,767,839 A | 6/1998 | Rosenberg |
| 7,113,166 B1 * | 9/2006 | Rosenberg ......... A63B 21/0057 |
| | | 345/156 |

(Continued)

OTHER PUBLICATIONS

"Geomagic Touch (formerly Geomagic Phantom Omni) Overview", Retrieved From <<http://www.geomagic.com/en/products/phantom-omni/overview>>, Retrieved on: Oct. 30, 2017, 2 Pages.

(Continued)

*Primary Examiner* — David Duffy
*Assistant Examiner* — Ankit B Doshi
(74) *Attorney, Agent, or Firm* — Medley, Behrens & Lewis, LLC

(57) ABSTRACT

A virtual reality system is described herein. The virtual reality system includes a cane controller and a computing system. The cane controller comprises a rod, a sensor, and a brake mechanism, wherein the sensor is configured to generate a signal that is indicative of position, direction of movement, and velocity of the rod, and wherein the brake mechanism is configured to apply a force to the rod. The computing system receives the signal, computes a position, direction of movement, and velocity of a virtual rod in a virtual space, and outputs a control signal to the brake mechanism based upon such computation. The brake mechanism applies the force to the rod in a direction and with a magnitude indicated in the control signal, thereby preventing the user from causing the virtual rod to penetrate a virtual barrier in the virtual space.

20 Claims, 8 Drawing Sheets

(51) Int. Cl.
*G06F 3/01* (2006.01)
*A63F 13/211* (2014.01)
(52) U.S. Cl.
CPC .............. *G06F 3/011* (2013.01); *G06F 3/016* (2013.01); *A63F 2300/8082* (2013.01)

(56) References Cited

U.S. PATENT DOCUMENTS

| 2005/0143173 | A1* | 6/2005 | Barney .................. A63F 13/428 463/37 |
|---|---|---|---|
| 2014/0168176 | A1 | 6/2014 | Nowatzyk et al. |
| 2018/0277292 | A1* | 9/2018 | Zarate .................. G09B 21/004 |
| 2018/0293980 | A1* | 10/2018 | Dwarakanath ............ A61F 9/08 |

OTHER PUBLICATIONS

"How Virtual Reality Facilitates Social Connection", Retrieved From <<https://www.facebook.com/iq/articles/how-virtual-reality-facilitates-social-connection>>, Jan. 9, 2017, 16 Pages.

"Igroup presence questionnaire (IPQ) Database", Retrieved From <<http://www.igroup.org/pq/ipq/data.php>>, Retrieved on: Oct. 30, 2017, 7 Pages.

"Long Cane Techniques, Study Guide: APH Step-by-Step", Retrieved From <<http://tech.aph.org/sbs/04_sbs_lc_study.html>>, Retrieved on: Oct. 30, 2017, 92 Pages.

"Novint—Products", Retrieved From <<http://www.novint.com/index.php/products>>, Retrieved on: Oct. 30, 2017, 3 Pages.

"Phantom Force Feedback", Retrieved From <<http://www.cgl.ucsf.edu/chimera/1.2470/docs/ContributedSoftware/phantom/phantom.html>>, Aug. 2005, 6 Pages.

Zyda, Michael, "From Visual Simulation to Virtual Reality to Games", In Journal of Computer, vol. 38, Issue 9, Sep. 2005, pp. 25-32.

Ando, et al., "A Contactless Haptic Cane for Blind People", In Proceedings of 12th joint symposium on Man Science and Measurement, Sep. 3, 2008, pp. 147-152.

Ando, et al., "A Haptic Solution to Assist Visually Impaired in Mobility Tasks", In Journal of IEEE Transactions on Human-Machine Systems, vol. 45, Issue 5, Oct. 2015, pp. 641-646.

Williams, et al., ""Pray Before You Step Out": Describing Personal and Situational Blind Navigation Behaviors", In Proceedings of the 15th International ACM SIGACCESS Conference on Computers and Accessibility, Oct. 21, 2013, 8 Pages.

Williams, et al., "Just let the cane hit it: how the blind and sighted see navigation differently", In Proceedings of the 16th international ACM SIGACCESS conference on Computers & accessibility, Oct. 20, 2014, pp. 217-224.

Bates, Joseph, "Virtual Reality, Art, and Entertainment", In Journal of Presence: Teleoperators and Virtual Environments, vol. 1, Issue 1, Jan. 2, 1992, pp. 1-9.

White, et al., "Toward accessible 3D virtual environments for the blind and visually impaired", In Proceedings of the 3rd international conference on Digital Interactive Media in Entertainment and Arts, Sep. 10, 2008, 8 Pages.

Borenstein, et al., "The GuideCane—a computerized travel aid for the active guidance of blind pedestrians", In Proceedings of IEEE International Conference on Robotics and Automation, Apr. 21, 1997, pp. 1-6.

Colwell, et al., "Haptic Virtual Reality for Blind Computer Users", In Proceedings of the third international ACM conference on Assistive technologies, Apr. 15, 1998, pp. 92-99.

Colwell, et al., "Use of a Haptic Device by Blind and Sighted People: Perception of Virtual Textures and Objects", In Publication of IOS Press, Jul. 1998, 8 Pages.

González-Mora, et al., "Development of a new space perception system for blind people, based on the creation of a virtual acoustic space", In Proceedings of International Work-Conference on Artificial Neural Networks, Jun. 2, 1999, 10 Pages.

González-Mora, et al., "Seeing the world by hearing: Virtual Acoustic Space (VAS) a new space perception system for blind people", In Journal of Information and Communication Technologies, Apr. 24, 2006, 6 Pages.

Wahab, et al., "Smart Cane: Assistive Cane for Visually-impaired People", In International Journal of Computer Science Issues, vol. 8, Issue 4, Jul. 2011, pp. 21-27.

Virvou, et al., "On the usability and likeability of virtual reality games for education: The case of VR-ENGAGE", In Journal of Computers and Education, vol. 50, Issue 1, Jan. 31, 2008, pp. 1-22.

Jack, et al., "Virtual Reality-Enhanced Stroke Rehabilitation", In Journal of IEEE Transactions on Neural Systems and Rehabilitation Engineering, vol. 9, No. 3, Sep. 2001, pp. 308-318.

Singh, et al., ""Smart" Cane for the Visually Impaired: Design and Controlled Field Testing of an Affordable Obstacle Detection System", In Proceedings of 12th International Conference on Mobility and Transport for Elderly and Disabled Persons, vol. 53, Issue 9, Jun. 2010, 13 Pages.

Jansson, et al., "Haptic virtual environments for blind people: exploratory experiments with two devices", In International Journal of Virtual Reality, vol. 3, No. 4, Retrieved on: Nov. 2, 2011, 2017, pp. 8-17.

Kalyvioti, et al., "Virtual Environments and Dyslexia: A Literature Review", In Journal of Procedia Computer Science, vol. 27, Dec. 2014, pp. 138-147.

Kawai, et al., "Evaluation of Interactive Tactile Display System", Retrieved From <<https://pdfs.semanticscholar.org/c8da/db1e1caa0b4e317db3bb8f22c6a45a52f8c6.pdf>> Retrieved on: Nov. 2, 2011, 8 Pages.

Kim, et al., "Drop-off Detection with the Long Cane: Effects of Different Cane Techniques on Performance", In Journal of visual impairment & blindness, vol. 103, Issue 9, Sep. 2009, pp. 1-14.

König, et al., "Haptic Exploration of Virtual Buildings Using Non-Realistic Haptic Rendering", In Proceedings of the 7th International Conference on Computers Helping People with Special Needs, Jul. 2000, 8 Pages.

Ulrich, et al., "The GuideCane—Applying Mobile Robot Technologies to Assist the Visually Impaired", In Journal of IEEE Transactions on Systems, Man, and Cybernetics,—Part A: Systems and Humans, vol. 31, No. 2, Mar. 2001, pp. 1-12.

Lahav, et al. "Exploration of Unknown Spaces by People Who Are Blind Using a Multi-sensory Virtual Environment", In Journal of Special Education Technology, vol. 19, Issue 3, Jun. 2004, pp. 15-23.

Lahav, et al., "Multisensory virtual environment for supporting blind persons' acquisition of spatial cognitive mapping, orientation, and mobility skills", In Proceedings of the Third International Conference on Disability, Virtual Reality and 4ssociated Technologies, Sep. 23, 2000, pp. 53-58.

Lécuyer, et al., "HOMERE: a Multimodal System for Visually Impaired People to Explore Virtual Environments", In Proceedings of IEEE Virtual Reality, Mar. 22, 2003, 8 Pages.

Maidenbaum, et al., "Increasing Accessibility to the Blind of Virtual Environments, Using a Virtual Mobility Aid Based on the "EyeCane": Feasibility Study", In Journal of PLoS One, vol. 8, Issue 8, Aug. 19, 2013, pp. 1-7.

Martin, et al., "The smart cane: An electrical engineering design project", In Proceedings of ASEE North Central Section Conference, Apr. 2009, pp. 1-9.

Menikdiwela, et al., "Haptic based walking stick for visually impaired people", In Proceedings of International conference on Circuits, Controls and Communications, Dec. 27, 2013, 7 Page.

Merabet, et al., "Audio-Based Navigation Using Virtual Environments: Combining Technology and Neuroscience", In Journal of Research and Practice in Visual Impairment and Blindness, vol. 2, Issue 3, Sep. 2009, pp. 128-137.

Merchant, et al., "Effectiveness of virtual reality-based instruction on students' learning outcomes in K-12 and higher education: A meta-analysis", In Journal of Computer Education, vol. 70, Jan. 2014, pp. 29-40.

Merians, et al., "Virtual Reality—Augmented Rehabilitation for Patients Following Stroke", In Journal of Physical Therapy, vol. 82, Issue 9, Sep. 2002, pp. 898-915.

(56) References Cited

OTHER PUBLICATIONS

Parsons, et al., "A Controlled Clinical Comparison of Attention Performance in Children with ADHD in a Virtual Reality Classroom Compared to Standard Neuropsychological Methods", In Journal of Child Neuropsychology, vol. 13, Issue 4, Jul. 2007, pp. 363-381.

Pascale, et al., "Bringing Haptics to Second Life for Visually Impaired People", In Proceedings of International Conference on Human Haptic Sensing and Touch Enabled Computer Applications, Jun. 10, 2008, pp. 1-10.

Picinali, et al., "Exploration of architectural spaces by blind people using auditory virtual reality for the construction of spatial knowledge", In International Journal of Human Computer Studies, vol. 72, Issue 4, Apr. 2014, pp. 393-407.

Reardon, Sara, "Playing by Ear", In Journal of Science, vol. 333, Issue 6051, Sep. 30, 2011, pp. 1816-1818.

Tzovaras, et al., "Interactive mixed reality white cane simulation for the training of the blind and the visually impaired", In Journal of Personal and Ubiquitous Computing, vol. 13, Issue 1, Jan. 2009, pp. 51-58.

Romano, et al., "Creating Realistic Virtual Textures from Contact Acceleration Data", In Journal of IEEE Transactions on Haptics, vol. 5 Issue 2, Apr. 2012, pp. 109-119.

Sánchez, et al., "Assisting the mobilization through subway networks by users with visual disabilities", In Proceedings of the Sixth International Conference on Disability, Virtual Reality and Associated Technologies, Sep. 18, 2006, pp. 183-190.

Sáanchez, et al., "Virtual Environment Interaction Through 3D Audio by Blind Children", In Journal of Cyberpsychology & behavior: the impact of the Internet, multimedia and virtual reality on behavior and society, vol. 2, No. 2, Feb. 1999, pp. 1-12.

Schloerb, et al., "BlindAid: Virtual environment system for self-reliant trip planning and orientation and mobility training", In Proceedings of IEEE Haptics Symposium, Mar. 25, 2010, pp. 363-370.

Schubert, et al., "The Experience of Presence: Factor Analytic Insights", In Journal of Presence: Teleoperators and virtual environments, vol. 10, Issue 3, Jun. 2001, pp. 266-281.

Seki, et al., "A training system of orientation and mobility for blind people using acoustic virtual reality", In Proceedings of IEEE Transactions on Neural Systems and Rehabilitation Engineering, vol. 19, Issue 1, Feb. 2011, pp. 35-104.

Semwal. S. K., "MoVE: Mobiltiy Training in Haptic Virtual Environment", Retrieved From <<https://pdfs.semanticscholar.org/243e/b3d64990f34d0b126b36132acc17e4f50737.pdf>>, Retrieved on: Oct. 30, 2017, pp. 1-18.

Sveistrup, Heidi, "Motor rehabilitation using virtual reality", In Journal of NeuroEngineering and Rehabilitation, vol. 1, Issue 1, Dec. 10, 2004, 8 Pages.

Choi, et al., "Wolverine: A Wearable Haptic Interface for Grasping in Virtual Reality", In Proceedings of IEEE/RSJ International Conference on Intelligent Robots and Systems, Oct. 9, 2016, 8 Pages.

"International Search Report and Written Opinion Issued in PCT Application No. PCT/US2018/061160", dated Feb. 20, 2019, 15 Pages.

Tatsumi, et al., "Cane Walk in the Virtual Reality Space Using Virtual Haptic Sensing", In Proceedings of International Conference on Systems, Man, and Cybernetics, Oct. 9, 2015, pp. 2360-2365.

Thaler, et al., "Mouth-clicks used by blind expert human echolocators—signal description and model based signal synthesis", In Journal of PLoS Computational Biology, vol. 13, No. 8, Aug. 31, 2017, pp. 1-17.

Tiponut, et al., "Acoustic Virtual Reality Performing Man-machine Interfacing of the Blind", In Proceedings of 12th WSEAS International Conference on Systems, Jul. 22, 2008, pp. 345-349.

Torres-Gil, et al., "Applications of Virtual Reality for Visually Impaired People", In Proceedings of WSEAS Transactions on Computers, vol. 9, Issue 2, Feb. 2010, pp. 184-193.

Tzovaras, et al., "Design and implementation of virtual environments training of the visually impaire", In Proceeding of the fifth international ACM conference on Assistive technologies, Jul. 8, 2002, pp. 41-48.

\* cited by examiner

APPARATUS FOR USE IN A VIRTUAL REALITY SYSTEM

BACKGROUND

Virtual reality (VR) technologies have been conventionally applied to fields such as entertainment (e,g., gaming), education, and social activities. Further, potential of VR has been recognized with respect to training and rehabilitation for people with disabilities, such as those with dyslexia, people who have experienced a stroke, people with attention-deficit hyperactivity disorder (ADHD), etc.

While VR applications have great potential in a variety of use cases, conventional VR applications rely upon realistic visual feedback to provide an immersive experience to sighted people, for whom the visual sense is dominant. These existing VR applications, however, are generally not accessible to people with visual impairments, thereby preventing such people from benefiting from VR technologies.

Prior work in VR that has been developed for use by people with visual impairments has focused on creating auditory VR—for instance, an audio-based environment simulator game has been developed that facilitate allowing blind users to interact with a virtual scene through auditory feedback. In such game, presence of objects is identified through sound rendering. For example, a conventional VR system employs an acoustic VR space, where a portable system generates spatial audio to create the illusion that objects in the virtual scene are covered with speakers emitting sounds depending on their physical characteristics (e.g., color, texture, etc.). In another exemplary conventional VR system, real-world navigation strategies of people with visual impairments are incorporated into a virtual space, where echolocation (use of sound reflecting off objects to localize them) is simulated in the virtual space to assist users in better understanding the virtual space.

Other conventional VR systems have introduced haptic sensations to provide benefits of VR to people with visual impairments. Haptic sensation by way of white canes is the main channel for people with visual impairments to understand a physical space, with audio serving as a channel for complementary information. When navigating the real-world, the white cane is commonly used for low resolution scanning of the environment and to detect obstacles and identify distances. Similarly, legs and feet are used to feel the ground surface, and the palm or fingers are used to precisely recognize the shape and texture of objects. In an exemplary conventional VR system, a joystick is employed by a user, where movement of the joystick corresponds to movement in a virtual space, and further where the joystick is vibrated to present cues to a user as to boundaries of the virtual space and virtual objects in the virtual space. This system, however, is unable to allow for natural movement of a user as the user navigates through the virtual space.

In yet another exemplary conventional VR system, a haptic glove is worn by a user and generates force feedback to fingers of the user as the user moves through a virtual space, thereby providing the illusion that the user is navigating the virtual space with a cane. The user can hold a real cane, the grasp posture of the user can be detected, and force feedback can be provided through the haptic glove (to simulate vibrations that would be felt based upon the tip of the cane impacting a virtual object in the virtual space). This real cane, however, penetrates virtual objects in the virtual space, thereby failing to provide a user with realistic proprioceptive feedback as the user employs the cane to navigate the virtual space.

SUMMARY

The following is a brief summary of subject matter that is described in greater detail herein. This summary is not intended to be limiting as to the scope of the claims.

Described herein are various technologies pertaining to a virtual reality (VR) system, wherein the VR system is well-suited for use by people with visual impairments. The VR system includes a computing system and an apparatus that is manipulated by a user of the VR system when navigating a virtual space. The computing system executes a VR application, wherein a VR environment (a virtual space) can be defined by way of the VR application. The virtual space can include barriers (such as walls), objects (such as tables, chairs, trash cans, etc.), steps, and so forth. Boundaries in the virtual space can also have materials assigned thereto, material thicknesses assigned thereto, colors assigned thereto, textures assigned thereto, etc. For instance, a floor in the virtual space can be carpeted, and accordingly is assigned a texture that corresponds to carpet; similarly, a floor in the virtual space can be tiled, and accordingly is assigned a texture that corresponds to ceramic. Still further, materials and textures in the virtual space are assigned audio characteristics. As will be described in greater detail herein, the computing system is configured to track movement of the user through the virtual space and interaction of the user with the virtual space based upon manipulation of the above-referenced apparatus by the user in the real-world.

The apparatus (referred to herein as a cane controller) includes a rod that comprises a proximal end and a distal end. In an example, the rod can have a length of between twelve inches and thirty-six inches. The proximal end of the rod is configured to be grasped by a hand of the user, and a sensor is coupled to the rod, wherein the sensor outputs a sensor signal that is indicative of position and orientation, direction of movement, and velocity of the distal end of the rod in the real-world (as the user manipulates the cane controller). The apparatus also includes a brake mechanism that is operably coupled to the rod, wherein the brake mechanism is configured to apply a resistive force to the rod, wherein magnitude and direction of the resistive force is based upon a control signal received from the computing system. The computing system generates such control signal based upon the signal output by the sensor that is coupled to the rod.

In an exemplary application, the computing system can construct a virtual cane of arbitrary length for use in the virtual environment, wherein position, velocity, and direction of movement of the virtual cane in the virtual space corresponds to position, velocity, and direction of movement of the rod in the real-world. Specifically, as location of the sensor on the rod is known, the computing system can receive the signal output by the sensor and compute a position, direction of movement, and velocity of any portion of the virtual cane (including the distal end of the virtual cane) based upon the sensor signal output by the sensor. When the VR application determines that the virtual cane impacts a surface (e.g., a wall, a virtual object, etc.) in the virtual space (based upon the signal output by the sensor and boundaries of the virtual space), the VR application can cause a control signal to be directed to the brake, wherein the brake applies resistive force such that the user (in the real-world) is unable to further move the rod. In other words, the virtual cane is prevented from penetrating boundaries in the virtual space. Thus, a user with a visual impairment navigating the virtual space will perceive physical boundaries as the user moves the rod about in the real-world (e.g., even though the virtual rod never impacts a real physical boundary).

The VR system described herein also can provide other channels of feedback to the user, including auditory feedback (e.g., three-dimensional spatial audio can be provided to the user by way of headphones), and a haptic mechanism can be coupled to the rod such that vibratory feedback is given to the user as the user navigates the virtual environment. For instance, when the virtual environment includes a carpeted floor, and the VR application determines that the distal end of the virtual cane is sweeping over and in contact with the carpet in the virtual space (e.g., where the determination is made based upon real-world manipulation of the rod by the user), the vibratory mechanism can provide vibratory feedback along the rod, where the vibratory feedback is configured to provide the user the sensation that a real cane is being moved over a real carpeted floor. The brake mechanism can also provide a force feedback as the distal end encounters friction with the carpet.

While the technologies have been described as well-suited for use by people with visual impairments, it is to be understood that the technologies described herein are not limited to such applications. For example, the technologies described herein may be well-suited for use with respect to physical rehabilitation, entertainment (gaming), etc. For instance, a virtual space may include a river, wherein the user is tasked with navigating the river in a kayak. The user may have one or more apparatuses attached thereto, wherein positions (including orientations), directions of movement, and velocities of oars in the virtual space are controlled by positions (including orientations), directions of movement, and velocities or rods manipulated by the user in the real-world. As an oar (controlled based upon movement of a rod) hits the water in the virtual space, the brake mechanism can be configured to provide viscous resistive force, thereby giving the user the sensation of additional resistance as the user is attempting to row through the virtual river.

In another exemplary application, the technologies described herein are well-suited for medical training. For instance, a surgeon can practice a surgery in a virtual environment, wherein position and movement of a distal end of the rod can be mapped to a virtual scalpel being held by the surgeon in a virtual surgery room. As the surgeon moves the rod in the real-world, such that the scalpel impacts skin of a virtual patient, the brake mechanism can be configured to emit resistive force to the rod, thereby giving the surgeon the perception of a change in resistance as the surgery is performed. In one or more of these applications, visual feedback can also be provided to enhance the experience in the virtual environment.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
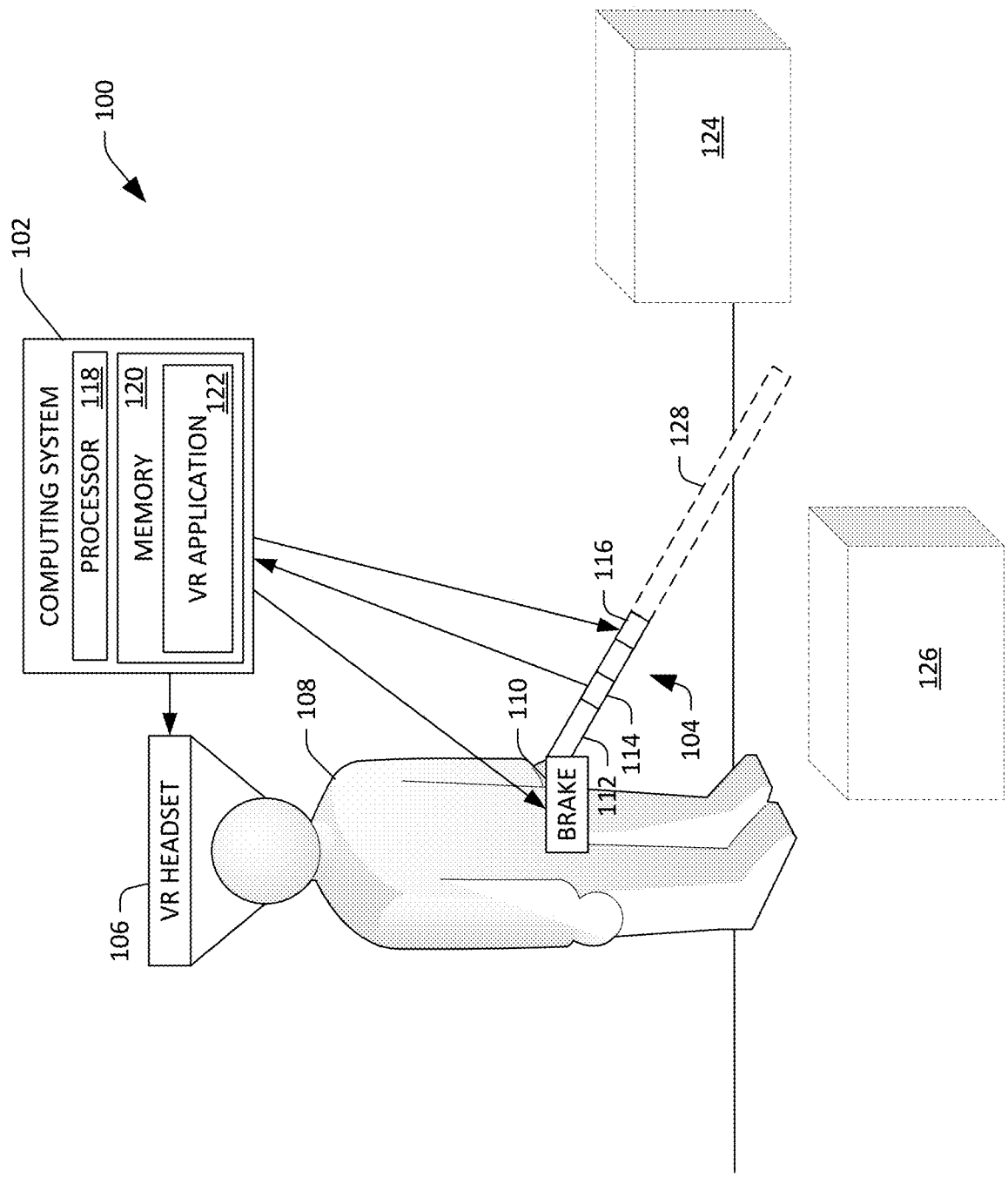
FIG. 1 is a schematic that depicts a virtual reality (VR) system that is well-suited for use by people with visual impairments.

Various technologies pertaining to a virtual reality (VR) system that is well-suited for use by people with visual impairments are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Described herein are various technologies pertaining to an apparatus, referred to herein as a cane controller, that is well-suited for allowing people with visual impairments to use real-world cane skills to explore virtual spaces. The cane controller described herein was inspired by real-world use of white canes by people with visual impairments. The cane controller provides three types of feedback: 1) braking; 2) vibrotactile; and 3) auditory. With respect to braking, when a virtual cane (controlled based upon movement of the cane controller) hits a virtual object in a virtual space, the brake mechanism generates physical resistance that prevents the cane controller, in the real-world, from further movement that would cause the virtual cane to penetrate boundaries of the object. Hence, with this proprioceptive feedback, the virtual cane does not penetrate virtual objects in the virtual space, thereby providing the user with the perception of boundaries of virtual objects in the virtual space.

With respect to vibrotactile feedback, when any part of the virtual cane contacts a virtual object (taps an object or sweeps over a surface of an object), the cane controller generates vibrotactile feedback to simulate the corresponding tap or texture vibration that the user would feel in the real-world if the user were interacting with real-world objects through use of a virtual cane.

With respect to auditory feedback, the VR system described herein can generate three-dimensional audio feedback and provide such audio to earphones being worn by a user to simulate the sound a real cane makes when impacting objects in the real-world (i.e., when the virtual cane impacts a metal trash can in the virtual space, three-dimensional audio feedback is provided that simulates the sound made when a real cane impacts a metal trash can in the real world, where the three-dimensional audio feedback can assist a blind user with localizing the sound in the virtual space) Sound rendering depends on the surface type and collision speed.

Using these different types of feedback, the VR system described herein supports at least three different cane strategies often employed by people with visual impairments: 1) shorelining; 2) two-point touch; and 3) constant contact.

Shorelining is a technique that uses touch and drag of a white cane to travel along an edge. A person can repeatedly tap the edge as the person travels along, moving the cane from the edge to the opposite side and then dragging the cane along the ground back toward the edge. In the VR system described herein, when a virtual cane hits a vertical surface, e.g., a virtual wall, in the horizontal left-right direction, the user can feel the physical resistance that enables them to perceive the boundary of the wall. The user can also feel the contact vibration and hear the 3-D sound, which simulates the collision between a real-world cane and wall. With this interaction, a person with a visual impairment can walk along a virtual wall with the cane controller described herein, by using shorelining techniques.

Two-point touch refers to swinging a cane from side to side and tapping the edges of a walking path on either side in an arc slightly wider than shoulders. Two-point touch is often used to protect both sides of a body of a walker. The cane controller described herein supports two-point touch, as when a virtual cane (controlled based upon the cane controller) taps on a surface, the cane controller generates corresponding vibration to simulate the tactile sensation. The user can also hear 3-D tapping sound from the VR system. With this interaction, the user can conduct two-point touch on different virtual surfaces, such as carpet, concrete, tactile domes, etc. by way of the cane controller.

Constant contact is a cane strategy that involves sweeping the cane from side to side and keeping the cane tip in contact with the surface at all times. This technique provides the most reliable detection of subtle surface changes at every point of the arc. Constant contact is supported by the VR system described herein, as the VR system generates resistive force, tactile and auditory feedback that simulates textures of different surfaces. Moreover, since tactile domes found at sidewalk crossings have bumps that would generate resistance when the cane sweeps across such bumps, the brake mechanism can be used to generate a short resistance at each bump, thereby providing the user with the illusion that a cane of the user hits the bumps. Further, the frequency and amplitude of the braking resistance can be modulated, as well as the vibrotactile feedback and the 3-D audio based on the virtual texture characteristics and sweeping speed of the cane controller.

With reference now to FIG. 1, a schematic that illustrates an exemplary virtual reality (VR) system 100 that is well-suited for use by people with visual impairments is illustrated. The VR system 100 and includes a computing system 102 and an apparatus 104 (referred to herein as a cane controller), wherein the cane controller 104 includes componentry that is in communication with the computing system 102. The VR system 100 optionally includes a VR headset 106. A user 108 can wear the VR headset 106 (which can include goggles that comprise one or more screens for depicting imagery and speakers positioned over or near the ears of the user 108). In an exemplary embodiment, the VR headset 106 can include the computing system 102. In other examples, the computing system 102 may be or include mobile telephone, a desktop computing device, a server computing device that is in network communication with the componentry of the cane controller 104, etc.

The cane controller 104 includes a brake mechanism 110 that is anchored to the body of the user 108. For example, the brake mechanism 110 may be coupled to a harness that is worn by the user 108, such that the brake mechanism 110 is positionally fixed at or near the abdomen of the user 108. The cane controller 104 additionally includes a rod 112 that is operably coupled to the brake mechanism 110. The brake mechanism 110 is configured to provide a resistive force to the rod 112, wherein the resistive force is in a direction that opposes the direction of force being applied to the rod 112 by the user 108. The brake mechanism 110 can be configured to apply such resistive force in one or more directions, where (as will be described below) magnitude(s) and direction(s) of resistive force(s) applied by the brake mechanism 110 can be based upon a magnitude and direction of force being applied to the rod 112 by the user 108. For instance, when the user 108 applies a leftward force to the rode 112 (with respect to the body of the user 108), the brake mechanism 110 can be configured to provide a resistive force in the rightward direction (or vice versa). Similarly, when the user 108 applies a downward force to the rod 112, the brake mechanism 110 can be configured to provide an upward force (and vice versa). Finally, when the user 108 applies a forward force (in the direction that the user 108 is looking), the brake mechanism 110 can be configured to provide force in the reverse direction (and vice versa). As will be described herein, the brake mechanism 110 is controlled by the computing system 102.

The cane controller 104 also includes a sensor 114 that is configured to output a sensor signal that is indicative of a position and orientation, direction of movement, and velocity of its 6DOF position. Therefore, the sensor 114 can be or include a 6DOF tracked sensor, an optical sensor, global positioning system (GPS) sensor, an accelerometer, a gyroscope, or other suitable inertial sensor. The cane controller 104 also includes a haptic device 116 that is configured to generate mechanical vibrations with controllable frequency and magnitude. In an exemplary embodiment, the rod 112 can be shorter than a conventional real-world cane, such as between twelve and thirty-six inches long. This shorter length reduces the possibility that the user 108, when manipulating the cane controller 104 in the real-world, will cause the cane controller 104 to come into physical contact with a real-world surface. In other embodiments, however, the rod 112 may have a length that is proximate to length of a real-world cane (e.g., about sixty inches).

The computing system 102 comprises a processor 118 and memory 120, wherein the memory has a VR application 122 loaded therein. The VR application 122, when executed by the processor 118, can construct a virtual space that is able to be navigated by the user 108, wherein the virtual space includes virtual boundaries and virtual objects that are analogous to real-world boundaries and objects. Accordingly, for instance, a virtual object and/or a virtual boundary can be assigned a material type, material width, texture, sound characteristics, etc. :In a more specific example, a virtual object that represents a trash can be assigned a material type of "metal", a material thickness of "0.1 inches", a texture of "ridged", and a sound characteristic (which may alter along a surface of the virtual object). In the example shown in FIG. 1, the VR application 122 generates a virtual space that includes two three-dimensional virtual objects 124 and 126. The VR application 122 is further configured to receive data from the VR headset 106 (e.g., generated by a sensor in the VR headset 106) that indicates a position and orientation of the head of the user 108 at any given time. The VR application 122 is further configured to receive signals output by the sensor 114 of the cane controller 104.

The VR application 122 employs signals received from the VR headset 106 to generate three-dimensional audio signals and cause such 3-D audio signals to be transmitted to the VR headset 106, which emits audio to the user by way of the speakers of the VR headset 106. The VR application 122 further receives signals generated by the sensor 114 and controls the brake mechanism 110 and the haptic device 116 based upon the signals output by the sensor 114. Moreover, the VR application 122 can employ the signal output by the sensor 114 to determine a position of the cane controller 104, and thus the user 108, in the virtual space constructed by the VR application 122.

Still further, when the cane controller 104 is designed to be shorter than a typical real-world cane, the VR application 122 can construct a virtual cane 128 that extends from the rod 104 by a distance that can be selected by the user 108 and/or based upon the height of the user 108, such that the virtual cane 128 has a length that is consistent with the length of a typical real-world cane (e.g., about sixty inches). In other words, as the length of the rod 112 is known, and as the position of the sensor 114 on the rod 112 is known, and further as the signal output by the sensor 112 is indicative of orientation of the rod 112, the VR application 122 can construct the virtual cane 128 such that the virtual cane 128 extends from the rod 112 at an appropriate distance. Further, the VR application 122 can compute a position, orientation, direction of movement, and velocity of a distal end of the virtual cane 128 based upon the signal output by the sensor 114.

Exemplary operation of the VR system 100 is now set forth. The user 108 places a VR headset 106 on her head, grasps the rod 112 of the cane controller 104, and causes the computing device 102 to execute the VR application 122, such that the VR space that includes the virtual objects 124 and 126 is constructed. The user 108 moves the rod 112 in the real-world as if using a cane, and the VR application 122 continuously constructs the virtual cane 128 based upon signals Output by the sensor 114, and additionally continuously computes position, orientation, direction of movement, and velocity of the distal end of the virtual cane 128 in the VR space based upon signals output by the sensor 112. For example, the user 108 can swing the rod 112 in a downward arc, and the VR application 122 can determine when the distal end of the virtual cane 128 impacts the ground in the virtual space (and speed of the virtual cane 128 at the time of impact) based upon signals output by the sensor 114.

When the VR application 122 determines that the distal end of the virtual cane 128 impacts the ground in the virtual space, the VR application 122 can cause a control signal to be transmitted to the VR headset 106, the brake mechanism 110, and/or the haptic device 116. The control signal, in an example, may cause the brake mechanism 110 to generate a resistive force in the upward direction, thereby preventing the user 108 from swinging the rod 104 further downward along the arc (and accordingly preventing the tip of the virtual cane 128 from penetrating the ground in the virtual space). The control signal, in another example, may cause the haptic device 116 to emit mechanical vibrations (such that the rod 112 is vibrated), such that the user 108 has the sensation of a real-world cane hitting a floor. The control signal, in yet another example, may cause speakers of the VR headset 106 to emit three-dimensional audio that simulates a tip of a real-world cane impacting a floor (where the floor has the texture defined in the virtual space), even though the distal end of the rod never impacts a real-world surface. In other words, the user 108 is provided with tactile and audio feedback as if the user 108 were using a real cane in the real-world and tapping a floor with the cane.

Continuing with this example, the user 108 may then begin sweeping the cane controller 104 in a horizontal direction, from left to right and right to left with respect to the body of the user 108, with the distal end of the rod 112 pointing towards the floor. In the virtual space constructed by the VR application 122, the distal end of the virtual cane 128 is swept across the floor while maintaining contact with the floor. Based upon signals generated by the sensor 114, the VR application 122 can compute a location of the distal end of the virtual cane 128 in the virtual space, and can control the brake mechanism 110, the haptic device 116, and/or the VR headset 106 based upon such signals. The VR application 122 can control the brake mechanism 110 such that the user 108 is prevented from pushing the distal end of the virtual cane 128 through the floor. The VR application 122 can control the haptic device 116 such that vibratory feedback is provided to the user 108, where such feedback is based upon the texture of the floor in the virtual space across which the distal end of the virtual cane 128 is being dragged. Based upon this vibratory feedback, the user 108 can understand whether the floor in the virtual space is carpeted, wooden, concrete, etc. The VR application 122 can control the VR headset 106 such that audio that simulates a cane being swept over a floor is provided to the user 108.

While sweeping the rod 112, the VR application 122 can determine that, for example, the distal end of the virtual cane 128 has impacted the surface of the virtual object 124 in the virtual space. Specifically, the VR application 122 receives signals output by the sensor 114 and determines that the distal end of the virtual cane 128 has impacted a surface of the virtual object 124 based upon the signals. The VR application 122 controls the brake mechanism 110, the haptic device 116, and/or the VR headset 106 responsive to determining that the distal end of the virtual cane 128 has impacted the surface of the virtual object 124 in the virtual space. As described previously, the VR application 122 can control the brake mechanism 110 such that the brake mechanism 110 applies a resistive force to the rod 112, thereby preventing the user 108 from further swinging the rod 112 along the horizontal arc in the leftward direction (thereby preventing the distal end of the virtual cane 128 from penetrating the virtual object 124). The VR application 122 controls the haptic device 116 to provide vibratory feedback to the user 108 based upon the material of the virtual object 124 and the velocity at which the distal end of the virtual cane 128 has impacted the surface of the virtual object 12.4 (as computed by the VR application 122). The VR application 122 controls the VR headset 106 such that the VR headset 106 emits audio that simulates a cane impacting an object in the real-world. From the foregoing, it can be ascertained that the user 108 is provided with feedback that emulates feedback that is perceived by the user 108 when interacting with real-world spaces when using a cane.

While the VR system 100 has been described as being well-suited for use by people with visual impairments, technologies of the VR system 100 are also well-suited for other applications, where users are not necessarily visually-impaired. For example, the technologies described herein are well-suited for physical therapy applications, athletic training applications, entertainment applications, and the like, wherein the VR application 122 can control the VR headset 106 to provide visual information to the user 108 as the user 108 navigates a virtual space. In an example, the technologies of the VR system 100 can be employed in a training scenario, where a surgeon employs the VR system 100 to practice a surgery in a virtual setting to train for the surgery in the real-world. For instance, the VR application 122 can construct a virtual space that includes a surgery table and a virtual patient, where an apparatus (akin to a real-world scalpel) is operably coupled to the rod 112. The VR application 122 can control the brake mechanism 110 to provide resistive feedback when a virtual scalpel (with orientation, location, direction of movement, and velocity mapping to user manipulation of the apparatus) impacts certain material (e.g., bone) of a virtual patient. Thus, the surgeon can undergo a realistic surgery simulation prior to performing the surgery on a real-world patient. In another example, the cane controller 104 can be used to control an oar in a virtual space where the user 108 is rowing in a kayak along a stream or lake. The VR application 122 can control the brake mechanism 110 to provide resistive force (modulated appropriately) when the oar impacts and travels through water. Further, in a game setting, the user 108 may be playing a game that includes a sword battle; the VR application 122 controls the brake mechanism 110 to provide resistive feedback when two swords clash in the environment (with the feedback provided as a function of computed velocity of the impact), such that virtual swords are unable to pass through each other. Other applications are readily ascertainable.

Figure 2:
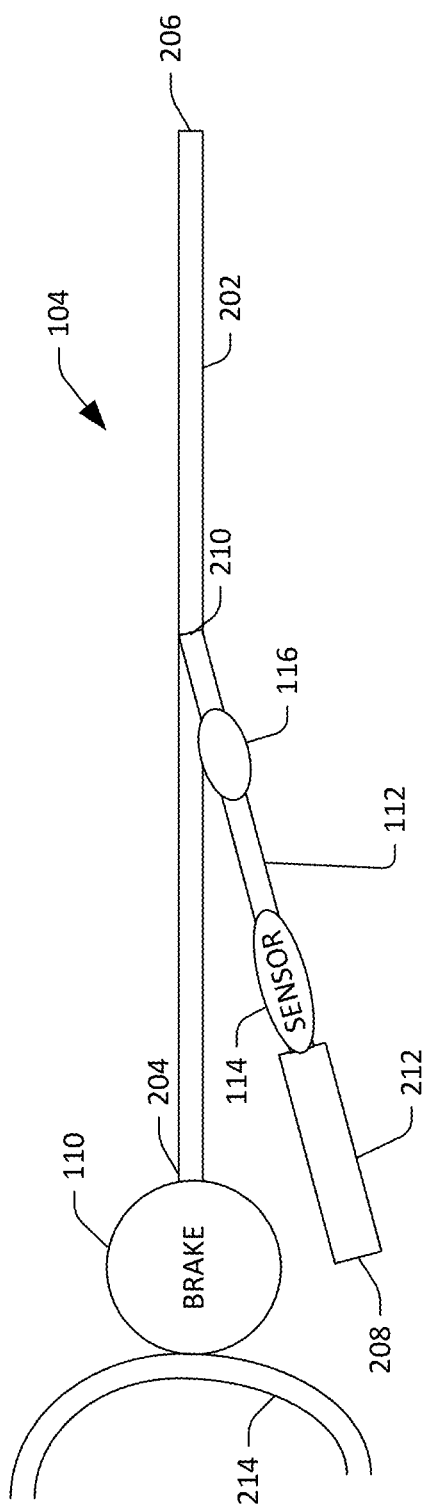
FIG. 2 illustrates an exemplary apparatus that is to be employed by a user of a VR system.

Now referring to FIG. 2, an exemplary implementation of the cane controller 104 is illustrated. The cane controller 104 comprises the rod 112, the sensor 114, the haptic device 116, and the brake mechanism 110. The cane controller 104 additionally includes a second rod 202 that is operably coupled to the brake mechanism 110 and the rod 112. The second rod 202 has a proximal end 204 and a distal end 206, wherein the proximal end 204 of the rod 202 is mechanically coupled to the brake mechanism 110. The rod 112 also includes a proximal end 208 and a distal end 210. The proximal end 208 of the rod 112 includes a handle 212 that is configured to be grasped by the user 108. The distal end 210 of the rod 212 is coupled to the second rod 202 and is slideable along a length of the second rod 202. The brake mechanism 110 is anchored to a body of the user by way of a harness 214.

In an example, the brake mechanism 110 can comprise a particle brake and/or a magneto theological brake, and can be mounted in a single-axis gimbal that is coupled to the harness 214 such that the brake mechanism 110 can freely rotate about an axis that is tangential to the abdomen of the user 108 and is parallel with the ground. In another example, the brake mechanism 110 can be mounted in a 2-axis gimbal such that the brake mechanism 110 can further rotate freely about a vertical axis. In yet another example, the brake mechanism 110 can include a ball and socket brake, wherein the handle 212 has a force/torque transducer therein that is in communication with the computing system 102. In such an exemplary embodiment, the transducer can output a signal that is indicative of an instantaneous force/torque direction being applied to the rod 112, and the computing system 102 can control the brake mechanism 110 such that the ball and socket brake applies a resistive force that is proportional to the force/torque being applied to the rod 112. Thus, the brake mechanism 110 is configured to provide resistive force to the second rod 202 based upon force applied by the user 108 to the second rod 202 by way of the rod 112. The resistive force provided by the brake mechanism 110 is a rotary force that prevents the second rod 202 from rotating about one or more axes that are positioned near a center of the brake mechanism 110.

As can be ascertained in FIG. 2, the haptic device 116 is positioned near the distal end 210 of the rod 112 while the sensor 114 is positioned near the handle 212, such that the sensor 114 is positioned between the proximal, end 208 of the rod 112 and the haptic device 116. The second rod 202 can have a length that is greater than a length of the rod 112. Accordingly, for instance, a length of the second rod 202 can be between twenty-four and forty-eight inches.

In an exemplary embodiment, the brake mechanism 110 and/or the haptic device 116 can include circuitry that is configured to receive control signals generated by the computing system 102 wirelessly from the computing system 102. Thus, the computing system 102 can transmit a control signal to the brake mechanism 110 and/or the haptic device 116 directly. In another exemplary embodiment, the cane controller 104 can comprise a control circuit that is in wired or wireless communication with the computing system 102 and acts as an interface between the computing system 102 and the brake mechanism 110 and/or the haptic device 116. For instance, the control circuit can be a microcontroller that is configured to receive a control signal from the computing system 102 and output signal(s) to the brake mechanism 110 and/or the haptic device 116 that cause the brake mechanism 110 and/or the haptic device 116 to operate in accordance with the control signal. Similarly, the sensor 114 can be configured to transmit a signal directly to the computing system 102, or can alternatively be configured to transmit a signal to a microcontroller on the cane controller 104, which is configured to transmit signals (by wire or wirelessly) to the computing system 102.

Additional detail relating to the brake mechanism 110 is now set forth As described previously, the brake mechanism 110 can be a resistive mechanism, which is configured to resist force in a direction perpendicular to the (rotary) brake shaft. To allow for the perception of force being applied in any suitable direction, the brake mechanism 110 can include three resistive brakes: a rotary brake and two brakes having a brake shaft, with each brake shaft connected to a lever arm at tight angles to the shaft. For any of the resistive brakes, this arrangement converts the rotary resistance torque of the brake to a linear force resistance at the end of the lever arm. The brakes in the brake mechanism 110 can be configured so that the brake mechanism 110 is able to apply forces in three (expected) resistance directions—sideways, up and down and "stabbing". Therefore, in FIG. 2, the three brakes act at three orthogonal directions with respect to the rod 202, wherein the rod is fixed to the brake mechanism 110. The computing system 102 receives signals output by the sensor 114, computes magnitude and direction of resistive forces to be applied to the rod by the brake mechanism 110, and geometrically translates such forces to control the brake mechanism 110, wherein the brake mechanism 110 is controlled to provide the user 108 with the perception that he or she is unable to penetrate virtual objects.

The two brakes with the brake shafts can be mounted in a two-axis gimbal, and account for resisting horizontal and vertical movements of the rod 202 (and thus the rod 112). The rotary brake can account for resisting "stabbing" movement of the virtual cane 128. In an example, two pulleys may be placed at the proximal end and the distal end of the rod 202, where a continuous string traverses between the two pulleys. One of the two pulleys is the rotary brake, such that the computing system 102 can control the tension applied to the string by the rotary brake based upon signals output by the sensor 114, wherein the signals are indicative of the sensed movement of the distal end 206 of the rod 112 along the rod 202. The tension represents resistance to force applied by the user in the "stabbing" direction. Other configurations of the brake mechanism 110 are also contemplated, wherein such configurations may include a force/torque sensor and a ball and socket brake, as referenced above.

Figure 3:
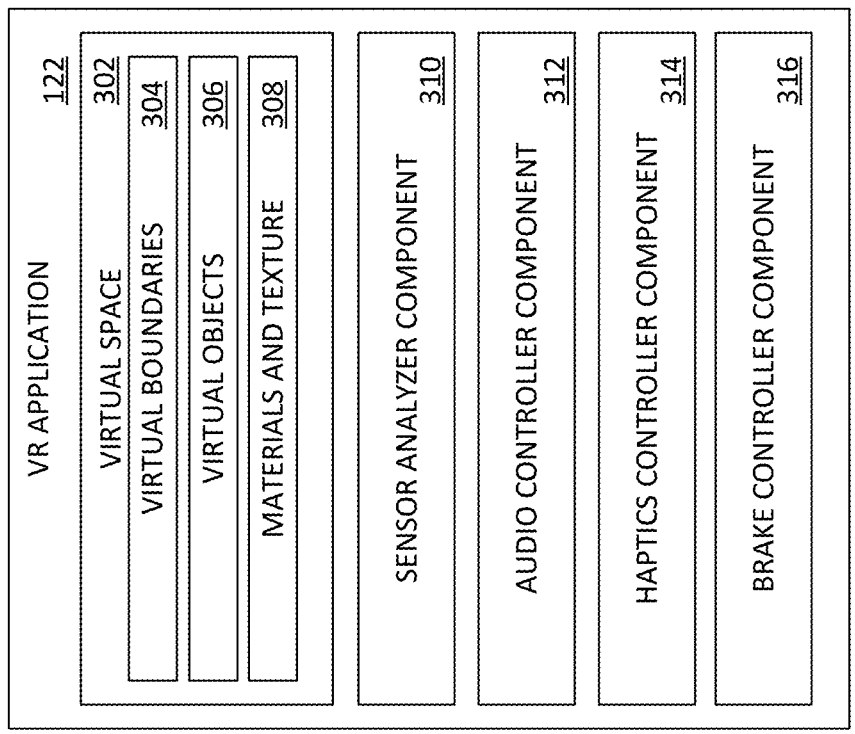
FIG. 3 is a functional block diagram of an exemplary VR application.

Now referring to FIG. 3, a functional block diagram of the VR application 122 is illustrated. The VR application 122 constructs a virtual space 302. The virtual space 302 includes virtual boundaries 304 (such as floors and walls), virtual objects 306 that exist in the virtual space 302 (such as tables, chairs, cans, etc.), and materials and texture 308 that is assigned to the virtual boundaries 304 and the virtual objects 306.

The VR application 122 further comprises a sensor analyzer component 310 that is configured to receive the signal generated by the sensor 114 and compute a location, orientation, direction of movement, and velocity of a distal end of the virtual cane 128 in the virtual space 302. The sensor analyzer component 310 computes the location, orientation, direction of movement, and velocity of the distal end of the virtual cane 128 based upon the signal generated by the sensor 114, a known location of the sensor 114 on the cane controller 104, and a desired length of the virtual cane 128.

The VR application 122 also includes an audio controller component 312 that causes three-dimensional audio to be provided to the user 108 based upon: 1) the location, orientation, direction of movement, and velocity of the distal end of the virtual cane 128 in the virtual space 302; and 2) a sensor signal from the VR headset 106 that is indicative of location and orientation of the ears of the user 108 (which is used to determine location and orientation of ears of the user 108 in the virtual space 302). Accordingly, the user 108 is provided with audio that can be used in connection with localizing an object in the virtual space 302, thereby simulating real-world auditory input employed by the user 108 when navigating real-world space.

The VR application 122 also comprises a haptics controller component 314 that controls the haptic device 116 of the cane controller 104 based upon signals output by the sensor 114. The haptics controller component 314 can control the haptic device 116 such that the user 108 is provided with vibro-tactile feedback that is indicative of texture of a surface being impacted by the distal end of the virtual cane 128, velocity at which the distal end of the virtual cane 128 has struck a virtual object in the virtual environment 302, and so forth. The haptics controller component 314 can cause the haptic device 116 to emit vibration with a frequency and amplitude that emulates frequency and amplitude felt by real-world cane users when navigating real-world spaces.

The VR application 122 also includes a brake controller component 316 that controls operation of the brake mechanism 110 based upon the signal output by the sensor 114 and locations of the virtual boundaries 304 and virtual objects 306 in the virtual space 302: As described above, the brake controller component 316 controls the brake mechanism 110 to prevent the virtual cane 128 from penetrating hard surfaces in the virtual space 302. The brake controller component 316 causes the brake mechanism 110 to generate a resistive force in a direction that opposes a direction of force being applied to the rod 112 of the cane controller 104 by the user 108.

Figure 4:
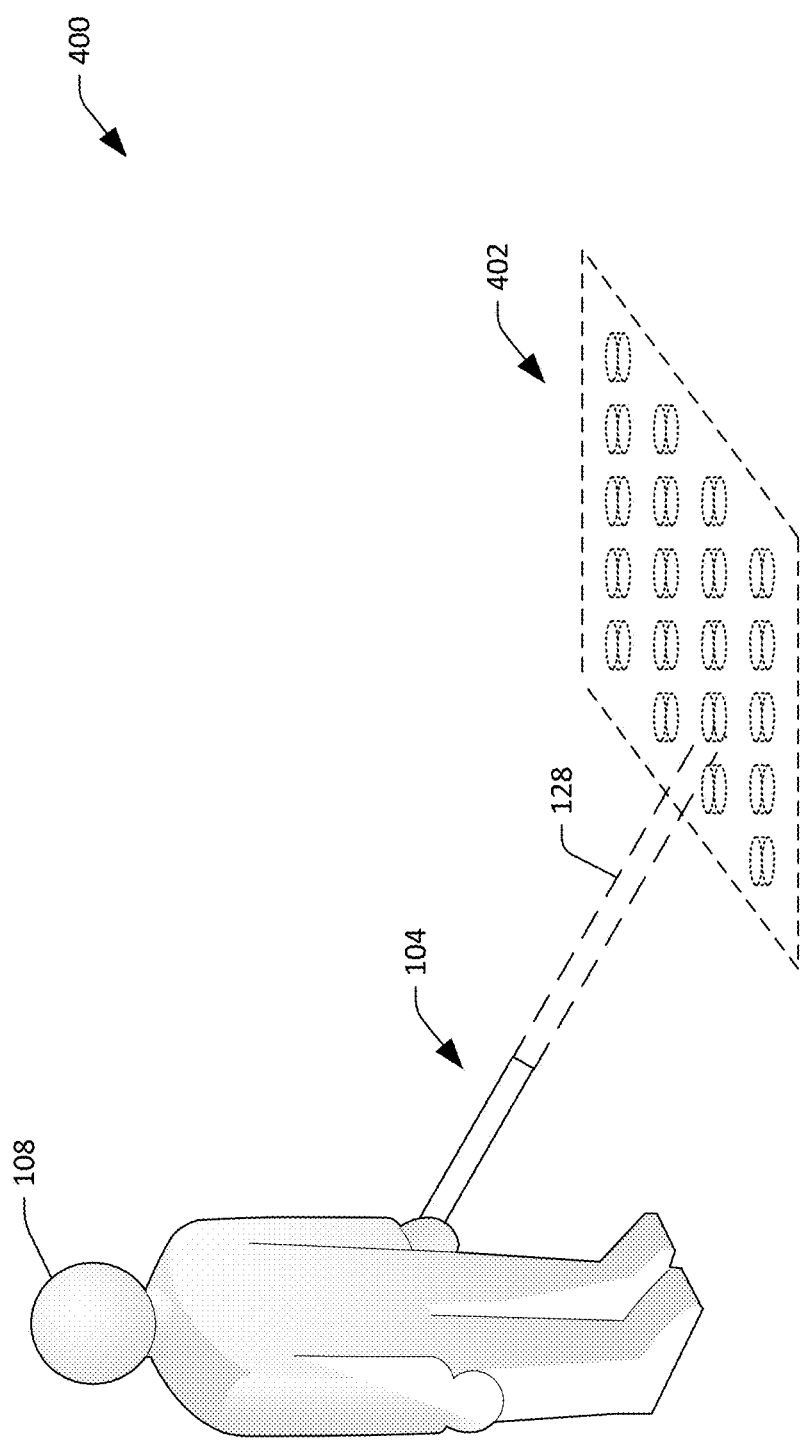
FIG. 4 is a schematic that depicts a user in a virtual space.

Now referring to FIG. 4, an exemplary virtual space 400 where the user 108 is employing the cane controller 104 is illustrated. In this example, in the virtual space 400, a distal end of the virtual cane 128 is moved over tactile domes 402 that are often found at street crossings. As the user 108 sweeps the virtual cane 128 over the tactile domes 402 in the virtual space, the brake mechanism 110 is modulated to give the user 108 the perception of the virtual cane 128 impacting walls of the tactile domes 402 as the virtual cane 128 sweeps over such domes. Thus, the brake controller component 316 can control the brake mechanism 110 such that resistive force is applied to the rod 112 as the user 108 sweeps the cane controller 104 horizontally and pointed downward at the ground. The haptics controller component 314 can also control the haptic device 116 to provide vibratory feedback, such that the user 108 perceives that a cane is vibrating as the tip of the virtual cane 128 travels over the tactile domes 402 in the virtual space 400.

Figure 5:
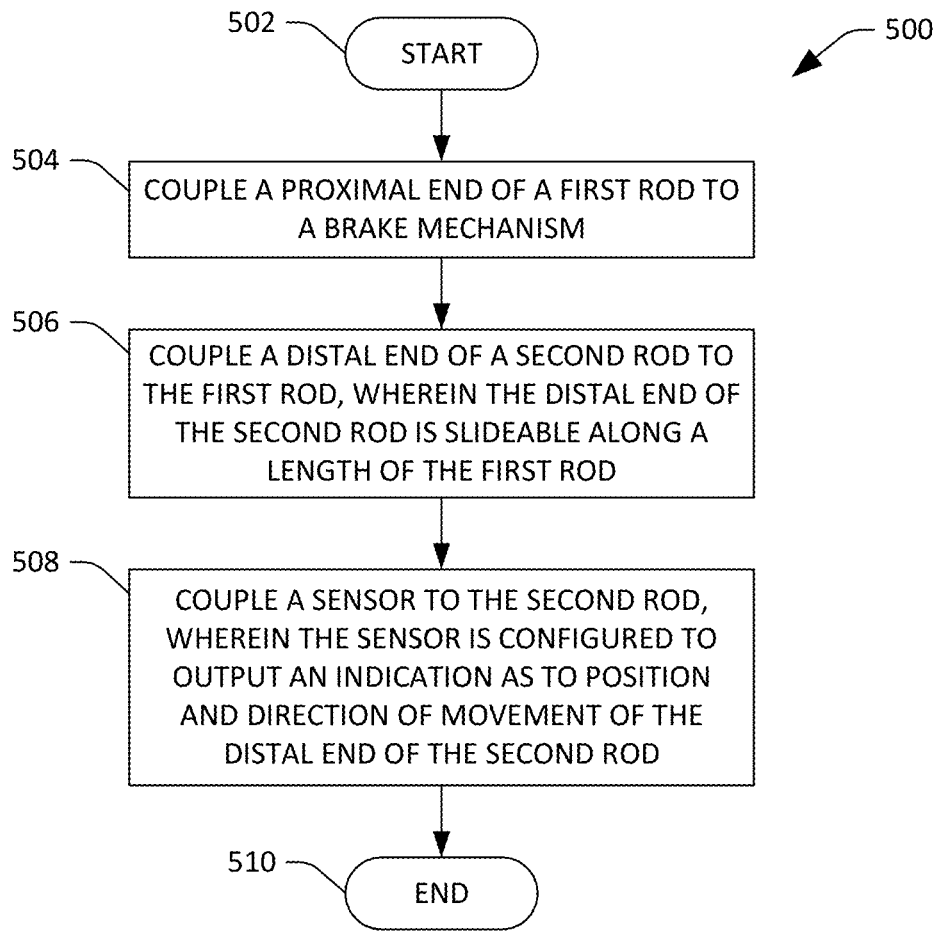
FIG. 5 is a flow diagram illustrating an exemplary methodology for configuring an apparatus that is well-suited for use in a virtual space.
Figure 6:
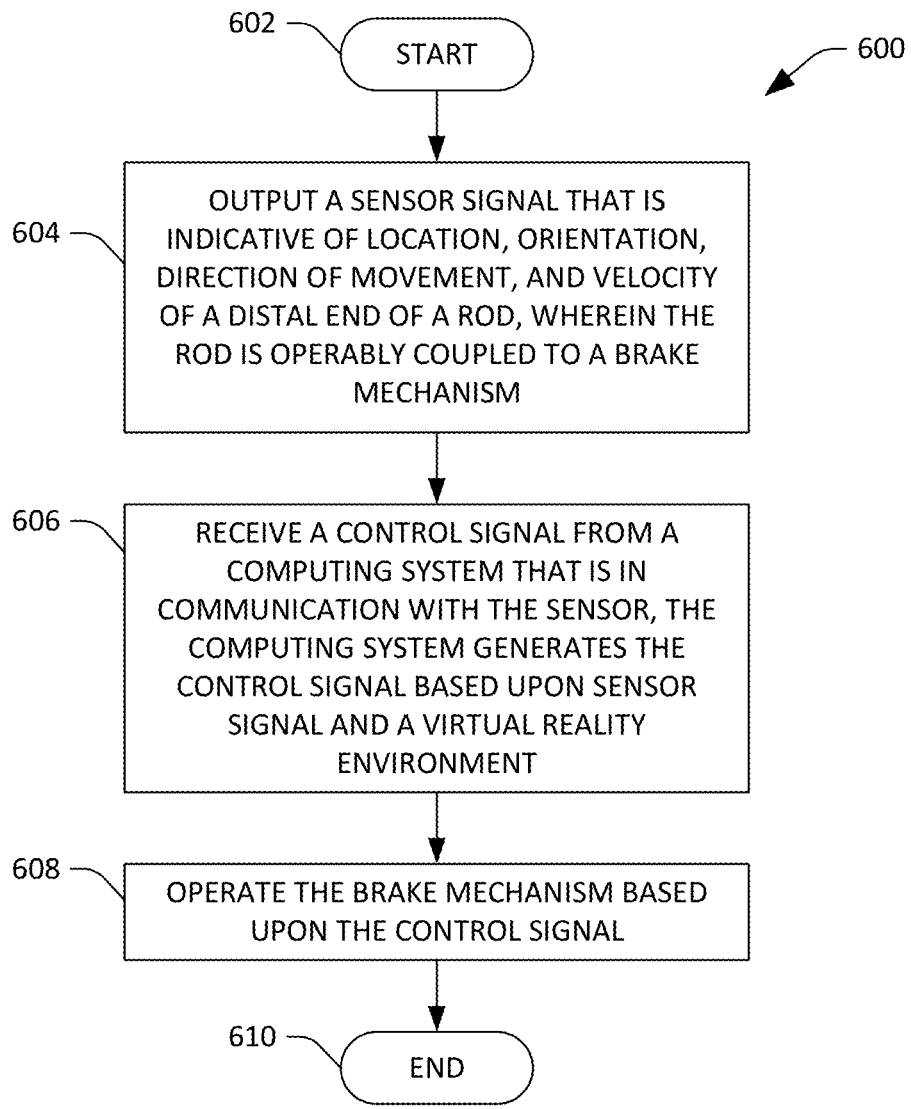
FIG. 6 is a flow diagram illustrating an exemplary methodology for controlling an apparatus that is to be used in a virtual space.
Figure 7:
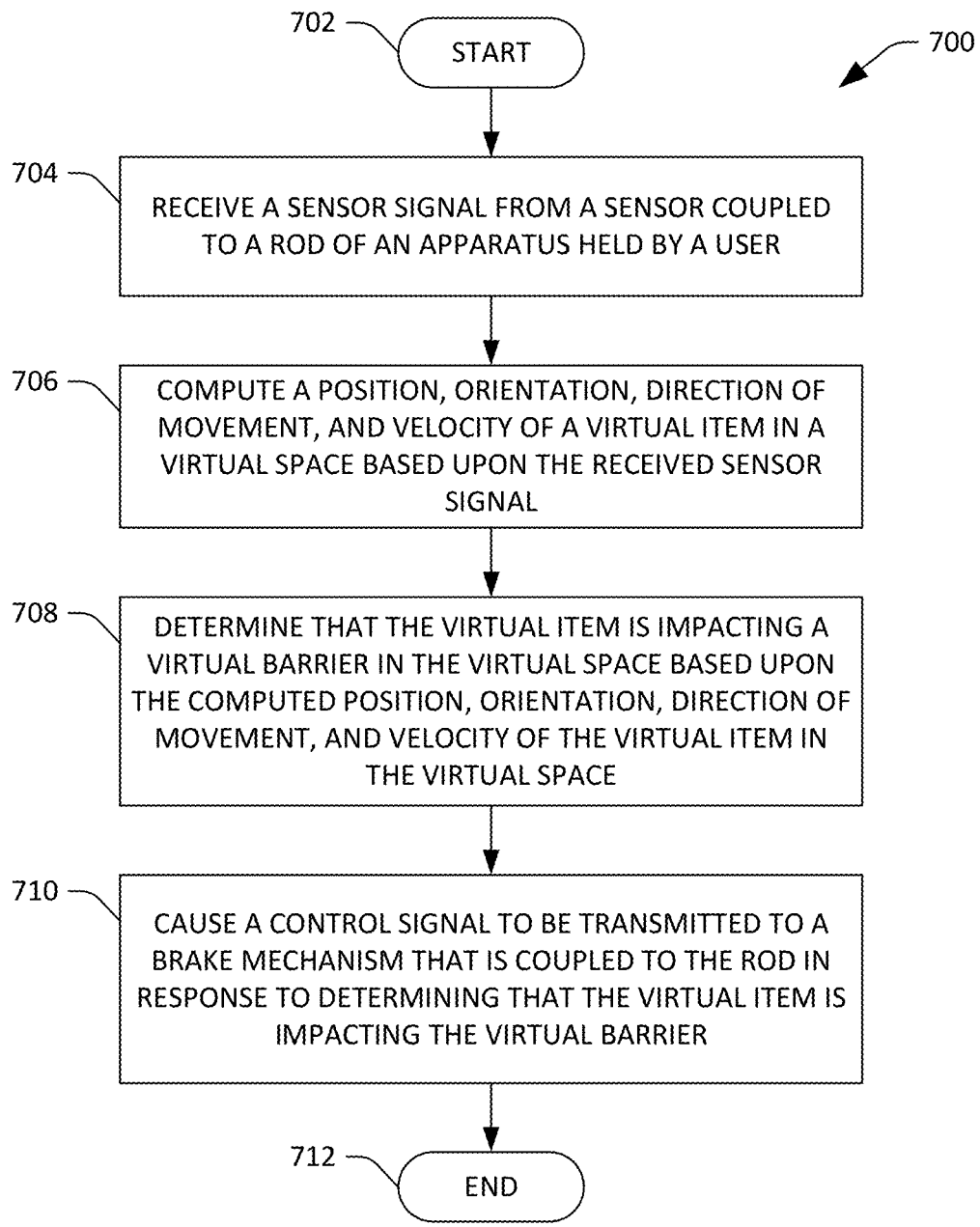
FIG. 7 is a flow diagram illustrating an exemplary methodology for controlling an apparatus that is used in virtual space.

FIGS. 5-7 illustrate exemplary methodologies relating VR applications. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Now referring to FIG. 5, an exemplary methodology 500 for configuring a cane controller is illustrated. The methodology 500 starts at 502, and at 504, a proximal end of a first rod is coupled to a brake mechanism, wherein the first rod has the proximal end and a distal end. At 506, a distal end of a second rod is coupled to the first rod, wherein the second rod has a proximal end and the distal end, with the proximal end being configured to be grasped by a user, and further wherein the distal end of the second rod is able to be slid along a length of the first rod. Further, the second rod is coupled to the first rod such that orientation of the second rod is able to alter with respect to the first rod based upon force applied to the second rod by the user. In the exemplary methodology 500, the first rod can be the rod 202 (described in FIG. 2 is being a second rod) and the second rod can be the rod 112.

At 508, a sensor is coupled to the second rod, wherein the sensor is configured to output an indication as to position and orientation, direction of movement, and velocity of the distal end of the second rod. Further, while not shown, optionally, a haptic device can be coupled to the second rod such that vibratory feedback can be provided to the user along the second rod. The methodology 500 completes at 510.

Now referring to FIG. 6, an exemplary methodology 600 performed by a cane controller as part of a VR system is illustrated. In an example, the methodology 600 can be performed by a microprocessor on the cane controller. In another example, acts of the methodologies can be performed by separate components of the cane controller. The methodology 600 starts at 602, and at 604, a sensor signal is output, where the sensor signal is based upon a signal generated by a sensor of the cane controller, and further wherein the sensor signal is indicative of location and orientation, direction of movement, and velocity of a distal end of a rod, wherein the rod is operably coupled to a brake mechanism. At 606, a control signal is received from a computing system that is in communication with the sensor, wherein the computing system generates the control signal based upon the sensor signal and a virtual space that a user of the cane controller is navigating. At 608, the brake mechanism is operated based upon the control signal. For example, the brake mechanism can be operated to simulate to the user that a virtual cane (controlled by the cane controller) has impacted a hard surface in the virtual space. The methodology 600 completes at 610.

With reference now to FIG. 7, an exemplary methodology 700 performed by a computing system that controls a cane controller is illustrated. The methodology 700 starts at 702, and at 704, a sensor signal is received from a sensor that is coupled to a rod of a cane controller, where the rod is manipulated by a user. At 706, a position, orientation, direction of movement, and velocity of at least a portion of a virtual item in a virtual space is computed based upon the received sensor signal. For instance, the virtual item can be a virtual cane. At 708, a determination is made that the virtual item is impacting a virtual barrier in the virtual environment, wherein the determination is made based upon the computed position, orientation, direction of movement, and velocity of the virtual item in the virtual space. At 710, a control signal is caused to be transmitted to a brake mechanism that is coupled to the rod in response to determining that the virtual item is impacting the virtual barrier. The methodology 700 completes at 712.

EXAMPLES

To build an exemplary cane controller, two pieces of a folding cane were combined to create a 24-inch cane controller. A PLACID industries magnetic particle brake (model B35) was used as the brake mechanism to generate resistive force, and a Dayton Audio® DAEX25FHE-4 voice coil was placed on the cane controller and used to generate mechanical vibration. The VR System used an HTC Vive® headset to track the head position of the user and generate 3-D audio feedback, and a Vive® tracker was attached to the cane controller to track its position. The VR System was implemented in the Unity® game engine.

The exemplary brake mechanism regards the body of the user as the anchor, allowing 360° rotation. The center of the brake mechanism was connected to the tip of the cane controller with a 35-inch slider. When the user sweeps the cane controller, the tip of the controller slides along the slider and drags the slider to rotate around the brake. A POLOLU motor controller 18v7 was used to control the brake mechanism. Fine grain adjustments to the flexibility of the brake shaft rotation can be made, and therefore an ease at which the user can sweep the cane controller can be controlled. When the brake mechanism is set to 100%, the brake shaft cannot rotate so that the user cannot sweep the cane controller without rotating his or her body. In the exemplary VR system, this is used to render hard body collisions, such as when the virtual cane hits a virtual object horizontally in the left-right direction. The brake mechanism is released when the tracker detects that the user starts to move the controller in the opposite direction. When the virtual cane sweeps on virtual tactile domes, the brake mechanism can be set to 30% in a short interval at each bump to simulate the resistance of hitting the bump.

To generate realistic vibrations upon collisions a POLOLU MiniIMU-9 v5 embedded with a LSM6DS33 3-axis gyro and accelerometer were attached to a real cane, and the acceleration data was recorded when a real cane came into contact with various objects. The equipped cane was used to hit different objects, such as a wall, a metal table, a plastic trash can, and sweep on different surfaces, such as carpet, concrete, and tactile domes, to record the corresponding acceleration data. When sweeping the cane on different surfaces, it was attempted to sweep with a relatively constant speed of 200 mm/s to reduce the effect of the hand motions on the acceleration data. The data was recorded at a sample rate of 1.4 kHz, The acceleration data was processed to generate an audio signal as the input of the voice coil. A high pass filter of 10 Hz was first used to remove the effect of unwanted forces, such as gravity in the accelerations from the researcher's hand motions when recording the data. Since human sensitivity to high-frequency vibrations is largely independent of direction, the 3-axis acceleration data was combined into a one-dimensional signal using a root sum square calculation, so that only one voice coil was needed. The signal was then multiplied with a constant factor to make it fit the input range of the voice coil. The signal was resampled from 1.4 kHz to 44.1 kHz, which is a standard audio sample rate, and the up-sampled audio was used as the output signal for the voice coil. The signal was amplified with a VELLEMAN MK190 amplifier to drive the voice coil, thereby making the vibrations stronger.

To generate realistic 3-D sound, a microphone was also attached to the tip of the cane to record the sound when the cane hit or sweep on different surfaces. The noises were removed in recorded sound with audio editing software, and the edited sound was used as an audio clip to play back when the virtual cane has a corresponding interaction in the virtual space. The sound was modulated depending on the speed of the virtual cane. The 3-D sound was rendered in Unity® using the Microsoft® Spatializer Plugin with a generic head rotation transfer function (HRTF).

Figure 8:
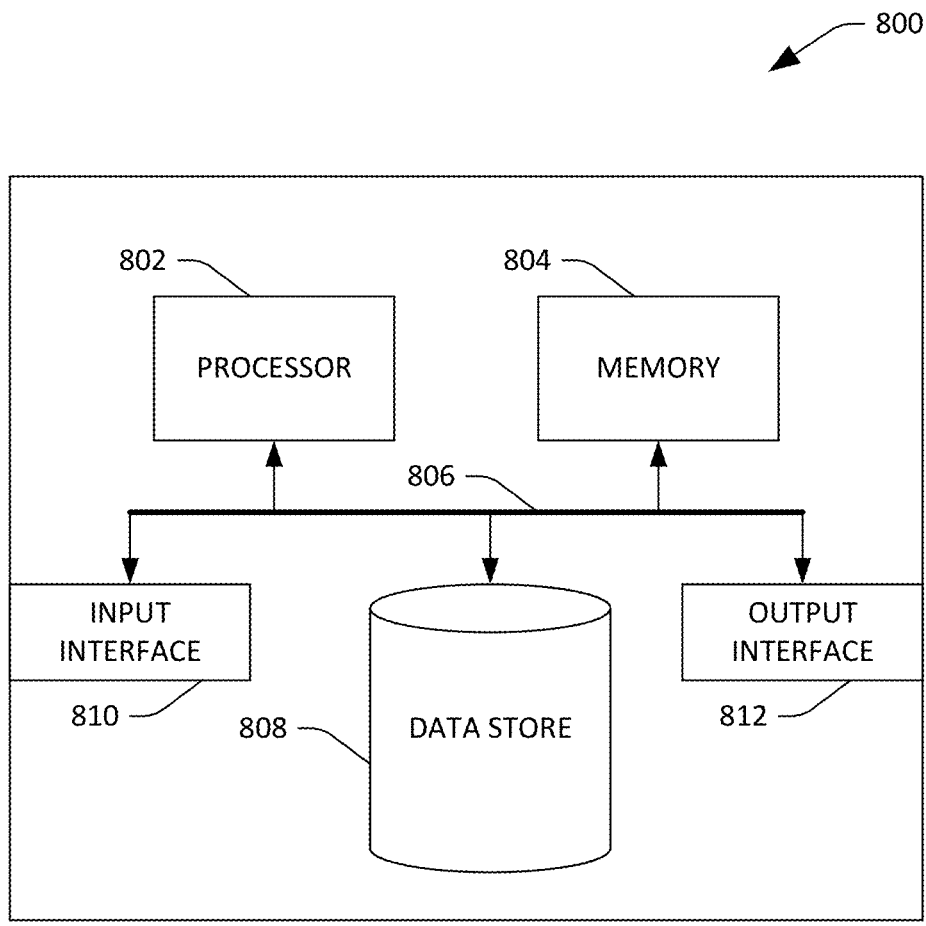
FIG. 8 is an exemplary computing system.

Referring now to FIG. 8, a high-level illustration of an exemplary computing device 800 that can be used in accordance with the systems and methodologies disclosed herein is illustrated. For instance, the computing device 800 may be used in a system that that supports controlling componentry of a cane controller. By way of another example, the computing device 800 can be used in a system that is configured to provide 3D audio to a user and/or detect orientation of a head of the user. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store sensor data, audio clips, imagery, etc.

The computing device 800 additionally includes a data store 808 that is accessible by the processor 802 by way of the system bus 806. The data store 808 may include executable instructions, pages, search logs, etc. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An apparatus that is configured for use in a virtual reality environment, the apparatus comprising:
    a brake mechanism;
    a first rod that has a first rod proximal end and a first rod distal end, wherein the first rod proximal is coupled to the brake mechanism;
    a second rod that has a second rod proximal end and a second rod distal end, wherein the second rod proximal end is configured to be grasped by a hand of a user, and further wherein the second rod distal end is coupled to the first rod such that the second rod distal end is slideable along the first rod between the first rod proximal end and the first rod distal end; and
    a sensor that is coupled to the second rod, wherein the sensor is configured to output a signal to a computing system that is indicative of a position, direction of movement, and velocity of the second rod distal end, and further wherein the computing system is configured to control the brake mechanism as a function of the signal output by the sensor.

2. The apparatus of claim 1, further comprising a haptic device that is coupled to the second rod, wherein the haptic device is configured to provide vibratory feedback to the hand of the user.

3. The apparatus of claim 2, wherein the sensor is positioned between the haptic device and the second rod proximal end.

4. The apparatus of claim 1, wherein the first rod has a length between twenty-four and forty-eight inches, and further wherein the second rod has a length between twelve and thirty-six inches.

5. The apparatus of claim 1, wherein a length of the first rod is greater than a length of the second rod.

6. The apparatus of claim 1, wherein the brake mechanism is configured to apply resistive forces to the first rod in three planes that are orthogonal to one another.

7. The apparatus of claim 1, further comprising a gimbal that is coupled to the brake mechanism, the gimbal facilitates free movement of the brake mechanism in a first plane, wherein the brake mechanism is configured to apply a rotary force to the first rod in a second plane that is orthogonal to the first plane.

8. The apparatus of claim 1, further comprising a force/torque sensor, wherein the brake mechanism comprises a ball and socket brake that is controlled based upon an output of the force/torque sensor.

9. The apparatus of claim 1, wherein the computing system comprises a virtual reality headset.

10. The apparatus of claim 1, wherein the computing system is one of a mobile telephone or a video game system.

11. An apparatus that is configured for use in a virtual reality environment, the apparatus comprising:
 a brake mechanism;
 a rod that is coupled to the brake mechanism, wherein the brake mechanism is configured to apply a resistive force to the rod, the resistive force opposes a force externally applied to the rod; and
 a sensor that is coupled to the rod, wherein the sensor is configured to output, to a computing system, a signal that is indicative of a position, direction of movement, and velocity of the rod, and further wherein the computing system is configured to control a magnitude of the resistive force applied to the rod by the brake mechanism based upon the signal that is output by the sensor.

12. The apparatus of claim 11, further comprising a second rod, wherein the second rod has a second rod proximal end and a second rod distal end, wherein the second rod proximal end is connected to the brake mechanism, and further wherein the rod is coupled to the brake mechanism by way of the second rod.

13. The apparatus of claim 12, wherein the rod has a first rod proximal end and a first rod distal end, wherein the first rod proximal end is configured to be grasped by a hand of a user of the apparatus, and wherein the first rod distal end is coupled to the second rod, the first rod distal end is slideable along a length of the second rod.

14. The apparatus of claim 13, further comprising a haptic device that is configured to generate mechanical vibrations along the rod, wherein the computing system is configured to control a magnitude of the mechanical vibrations based upon the signal that is output by the sensor.

15. The apparatus of claim 14, wherein the sensor is positioned between the haptic device and the first rod proximal end.

16. The apparatus of claim 11, wherein the rod has a length that is between twelve inches and thirty-six inches.

17. An apparatus that is configured for use in a virtual reality system, the apparatus comprising:
 a rod;
 braking means for applying a force to the rod; and
 sensor means for outputting a signal that is indicative of a location, direction of movement, and velocity of a distal end of the rod, wherein a computing system is configured to receive the signal and transmit a control signal to the braking means based upon the signal, wherein the control signal indicates a magnitude of the force that is to be applied to the rod by the braking means, and further wherein the braking means applies the force with the magnitude indicated in the control signal.

18. The apparatus of claim 17, further comprising vibration means coupled to the rod, the vibration means configured to generate vibrations along the rod based upon a second control signal received from the computing system.

19. The apparatus of claim 17, further comprising a force/torque sensor, wherein the braking means comprises a ball and socket brake that is controlled based upon output of the force/torque sensor.

20. The apparatus of claim 17, wherein the braking means comprises at least one of a particle brake or a magneto rheological brake.

\* \* \* \* \*